(12) United States Patent
Malinin et al.

(10) Patent No.: US 11,944,389 B2
(45) Date of Patent: Apr. 2, 2024

(54) IMPEDANCE SHIFT AND DRIFT DETECTION AND CORRECTION

(71) Applicant: St. Jude Medical, Cardiology Division, Inc., St. Paul, MN (US)

(72) Inventors: Yuriy Malinin, Edina, MN (US); Anthony D. Hill, Minneapolis, MN (US); Cable P. Thompson, St. Paul, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 627 days.

(21) Appl. No.: 16/662,737

(22) Filed: Oct. 24, 2019

(65) Prior Publication Data

US 2020/0121401 A1    Apr. 23, 2020

Related U.S. Application Data

(63) Continuation of application No. 15/187,322, filed on Jun. 20, 2016, now Pat. No. 10,492,869.
(Continued)

(51) Int. Cl.
*A61B 34/20* (2016.01)
*A61B 5/00* (2006.01)
(Continued)

(52) U.S. Cl.
CPC .............. *A61B 34/20* (2016.02); *A61B 5/062* (2013.01); *A61B 5/063* (2013.01); *A61B 5/066* (2013.01);
(Continued)

(58) Field of Classification Search
None
See application file for complete search history.

(56) References Cited

U.S. PATENT DOCUMENTS

| 6,104,944 A | 8/2000 | Martinelli |
| 6,233,476 B1 | 5/2001 | Strommer et al. |

(Continued)

FOREIGN PATENT DOCUMENTS

| CN | 1903122 A | 1/2007 |
| CN | 101449292 A | 6/2009 |

(Continued)

OTHER PUBLICATIONS

"Communication Pursuant to Article 94(3) EPC dated Sep. 20, 2022", 8 Pages.
(Continued)

*Primary Examiner* — Jonathan Cwern
(74) *Attorney, Agent, or Firm* — Billion & Armitage

(57) ABSTRACT

An impedance location of an electrode in an impedance based coordinate system and a magnetic location of a magnetic position sensor in a magnetic based coordinate system can be received. A transformed impedance location of the magnetic position sensor can be computed. A difference between the transformed impedance location of the magnetic position sensor and the magnetic location of the magnetic position sensor can be determined. A magnitude of the difference between the impedance location of the magnetic position sensor and the magnetic location of the magnetic position sensor can be computed. A statistical significance of the difference between the transformed impedance location of the magnetic position sensor and the magnetic location of the magnetic position sensor can be computed. A determination can be made that an impedance shift exists if the magnitude of the difference exceeds a threshold and a statistical significance of the difference exceeds a threshold.

8 Claims, 4 Drawing Sheets

Related U.S. Application Data

(60) Provisional application No. 62/182,208, filed on Jun. 19, 2015.

(51) Int. Cl.
  *A61B 5/06* (2006.01)
  *A61M 25/01* (2006.01)
  *A61B 1/00* (2006.01)

(52) U.S. Cl.
  CPC .......... *A61B 5/068* (2013.01); *A61B 5/7221* (2013.01); *A61M 25/0127* (2013.01); *A61B 1/00158* (2013.01); *A61B 5/7203* (2013.01); *A61B 5/7264* (2013.01); *A61B 2034/2053* (2016.02); *A61B 2034/2065* (2016.02); *A61M 2025/0166* (2013.01)

(56) References Cited

U.S. PATENT DOCUMENTS

| | | |
|---|---|---|
| 7,197,354 B2 | 3/2007 | Sobe |
| 7,263,397 B2 | 8/2007 | Hauck et al. |
| 7,386,339 B2 | 6/2008 | Strommer et al. |
| 7,536,218 B2 | 5/2009 | Govari et al. |
| 8,744,599 B2 | 6/2014 | Tegg |
| 2007/0060833 A1 | 3/2007 | Hauck |
| 2007/0073179 A1 | 3/2007 | Afonso et al. |
| 2007/0268287 A1 | 11/2007 | Magnin et al. |
| 2008/0161681 A1 | 7/2008 | Hauck |
| 2009/0205403 A1 | 8/2009 | Boese et al. |
| 2011/0105897 A1 | 5/2011 | Kornblau et al. |
| 2011/0158488 A1 | 6/2011 | Cohen |
| 2011/0176746 A1* | 7/2011 | Bucki .................. G06T 7/30 382/293 |
| 2011/0313414 A1 | 12/2011 | Liu et al. |
| 2012/0004533 A1* | 1/2012 | Peng .................. A61B 6/487 600/424 |
| 2012/0172702 A1 | 6/2012 | Koyrakh et al. |
| 2012/0265054 A1* | 10/2012 | Olson .................. A61B 90/39 600/424 |
| 2012/0302869 A1 | 11/2012 | Koyrakh et al. |
| 2013/0066193 A1* | 3/2013 | Olson .................. A61B 5/062 600/424 |
| 2013/0211206 A1 | 8/2013 | Sands et al. |
| 2013/0267835 A1 | 10/2013 | Edwards |
| 2014/0221803 A1 | 8/2014 | Bar-Tal et al. |
| 2014/0275957 A1 | 9/2014 | Lupotti |
| 2016/0367168 A1 | 12/2016 | Malinin et al. |

FOREIGN PATENT DOCUMENTS

| | | |
|---|---|---|
| CN | 103025242 A | 4/2013 |
| CN | 103687533 A | 3/2014 |
| CN | 103813748 A | 5/2014 |
| CN | 104290730 A | 1/2015 |
| EP | 2168478 A1 | 3/2010 |
| EP | 2233070 B1 | 2/2012 |
| JP | 2007021218 A | 2/2007 |
| JP | 2014064922 A | 4/2014 |
| JP | 2014511737 A | 5/2014 |
| JP | 2014530030 A | 11/2014 |
| JP | 2018519046 A | 7/2018 |
| WO | 2007135609 A2 | 11/2007 |
| WO | 2012001365 A1 | 1/2012 |
| WO | 2012141775 A1 | 10/2012 |
| WO | 2013039564 A2 | 3/2013 |
| WO | 2014028114 A1 | 2/2014 |
| WO | 2015085011 A1 | 7/2016 |
| WO | 2016205807 A1 | 12/2016 |
| WO | 2016205809 A1 | 12/2016 |

OTHER PUBLICATIONS

"Notice of Reasons for Rejection dated Sep. 20, 2022", 3 Pages.
"Regularization (mathematics)", Oct. 29, 2018, 11 pages.
Bourmaud, Guillaume , et al., "From Intrinsic Optimization to Iterated Extended Kalman Filtering on Lie Groups", J Math Imaging Vis, Jan. 2, 2016, 284-303.
Karlgaard, Christopher D, "Nonlinear Regression Huber-Kalman Filtering and Fixed-Interval Smoothing", Journal of Guidance, Control, and Dynamics, Jan. 8, 2015, 9 pages.

* cited by examiner

IMPEDANCE SHIFT AND DRIFT DETECTION AND CORRECTION

CROSS-REFERENCE TO RELATED APPLICATION

This application is related to the application PCT/US: 2016/038402 entitled "IMPEDANCE SHIFT AND DRIFT DETECTION AND CORRECTION", filed 20 Jun. 2016. This application is a continuation of U.S. patent application Ser. No. 15/187,322, now U.S. Pat. No. 10,492,869 which claims priority to U.S. provisional patent application No. 62/182,208 entitled "IMPEDANCE SHIFT AND DRIFT DETECTION AND CORRECTION", filed 19 Jun. 2015, which are hereby incorporated by reference as though fully set forth herein.

BACKGROUND a. Field

The present disclosure relates generally to impedance shift and drift detection and correction.

b. Background

The three-dimensional coordinates of a catheter or other medical device moving within a patient's body are often tracked using a localization system (sometimes also referred to as a "mapping system," "navigation system," or "positional feedback system"). These devices typically use magnetic, electrical, ultrasound, and other radiation sources to determine the coordinates of these devices. For example, impedance-based localization systems determine the coordinates of the medical device by interpreting a voltage measured by the medical device as a location within an electrical field.

Each different type of localization system offers certain advantages and disadvantages. For example, an impedance-based localization system offers the ability to track numerous localization elements simultaneously, but is susceptible to inhomogeneities in the electrical field and shift and/or drift resulting from varying impedance regions and other external factors. Likewise, a magnetic-based system offers the advantages of improved homogeneity and less drift than an impedance-based system. Such systems, however, require special sensors to be used as localization elements and, as such, are relatively limited in the number of localization elements that can be simultaneously tracked.

SUMMARY

Various embodiments herein provide a method for detection of an impedance shift in an impedance based coordinate system. An impedance location of an electrode in an impedance based coordinate system and a magnetic location of a magnetic position sensor in a magnetic based coordinate system can be received. A transformed impedance location of the magnetic position sensor can be computed using an electromagnetic registration between the impedance based coordinate system and the magnetic based coordinate system. A difference between the transformed impedance location of the magnetic position sensor and the magnetic location of the magnetic position sensor can be determined. A magnitude of the difference between the impedance location of the magnetic position sensor and the magnetic location of the magnetic position sensor can be computed. A statistical significance of the difference between the transformed impedance location of the magnetic position sensor and the magnetic location of the magnetic position sensor can be computed. A determination can be made that an impedance shift exists if the magnitude of the difference exceeds a threshold and a statistical significance of the difference exceeds a threshold.

Various embodiments herein provide a method for correction of an impedance shift in an impedance based coordinate system. A shifted impedance location of an electrode in a shifted impedance based coordinate system can be received. An electromagnetic registration can be applied to transform the shifted impedance location of the electrode from the shifted impedance based coordinate system into a shift corrected location of the electrode in the magnetic based coordinate system, using the electromagnetic registration.

Various embodiments herein provide a non-transitory computer-readable medium storing instructions for detection and correction of an impedance shift in an impedance based coordinate system. An impedance location of an electrode in an impedance based coordinate system and a magnetic location of a magnetic position sensor in a magnetic based coordinate system can be received. A transformed impedance location of the magnetic position sensor can be computed using a first electromagnetic registration between the impedance based coordinate system and the magnetic based coordinate system. A difference between the transformed impedance location of the magnetic position sensor and the magnetic location of the magnetic position sensor can be determined. A determination can be made that an impedance shift exists based on the difference between the transformed impedance location of the magnetic position sensor and the magnetic location of the magnetic position sensor. A second electromagnetic registration can be applied, in response to the determination that the impedance shift exists, to transform the impedance location of the electrode from a shifted impedance based coordinate system into a shift corrected location of the electrode in the magnetic based coordinate system, using the second electromagnetic registration.

DETAILED DESCRIPTION

Figure 1:
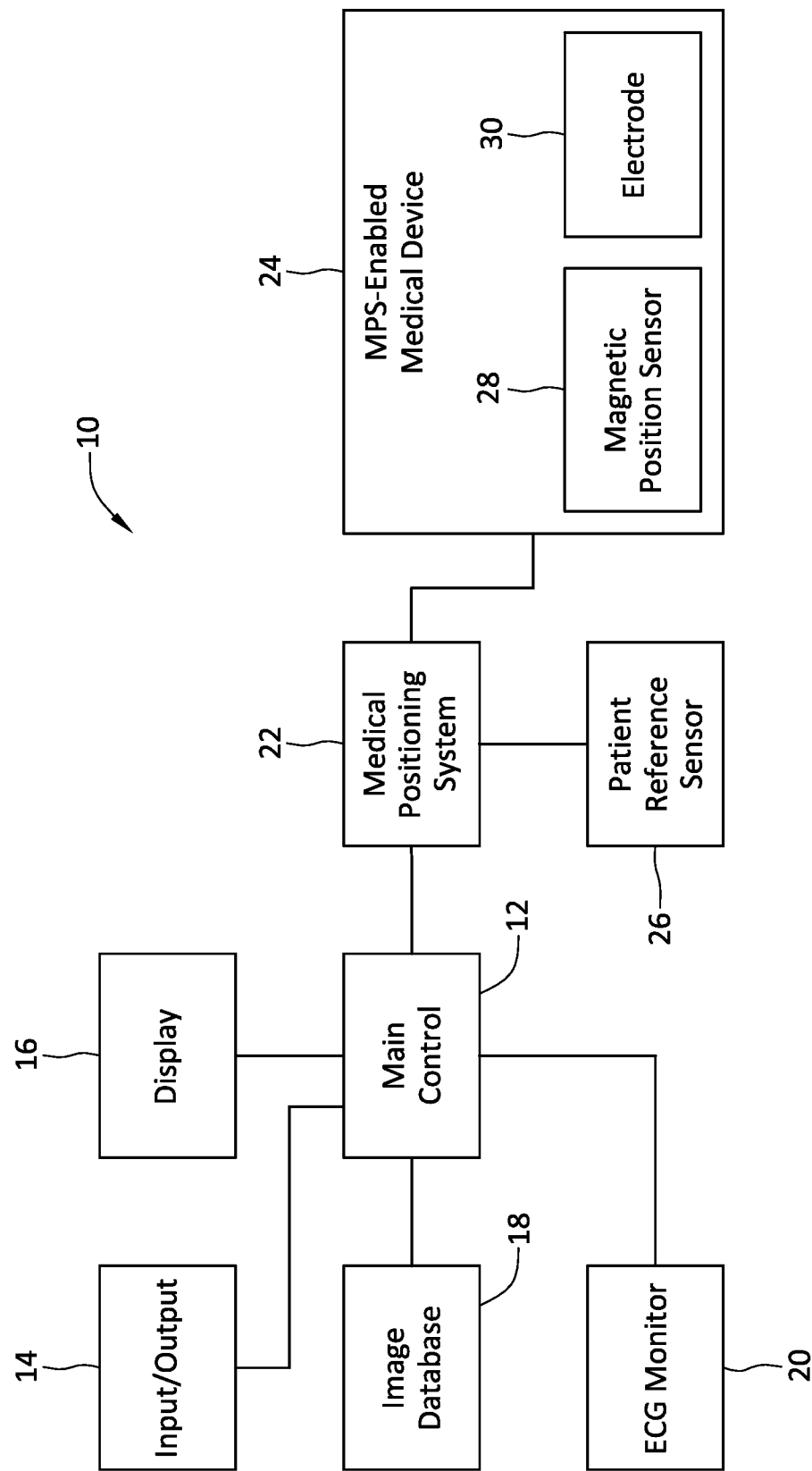
FIG. 1 depicts a schematic and block diagram view of an electromagnetic navigation system, in accordance with embodiments of the present disclosure.

Referring now to the drawings wherein like reference numerals are used to identify identical or similar components in the various views, FIG. 1 is a diagrammatic view of a system 10 in which a medical device, such as a guidewire, catheter, introducer (e.g., sheath) incorporating an magnetic position sensor 28 and an electrode 30 may be used.

Before proceeding to a detailed description of the embodiments of the present disclosure, a description of an exemplary environment in which such devices and sensors may be used will first be set forth. With continued reference to FIG. 1, system 10, as depicted, includes a main electronic control unit 12 (e.g., a processor) having various input/output mechanisms 14, a display 16, an optional image database 18, an electrocardiogram (ECG) monitor 20, a localization system, such as a medical positioning system 22, a medical positioning system-enabled elongate medical device 24, a patient reference sensor 26, a magnetic position sensor 28 and an electrode 30. For simplicity, one magnetic position sensor 28 and one electrode 30 are shown, however, more than one magnetic position sensor 28 and/or more than one electrode 30 can be included in the system 10.

Input/output mechanisms 14 may comprise conventional apparatus for interfacing with a computer-based control unit including, for example, one or more of a keyboard, a mouse, a tablet, a foot pedal, a switch and/or the like. Display 16 may also comprise conventional apparatus, such as a computer monitor.

Various embodiments described herein may find use in navigation applications that use real-time and/or pre-acquired images of a region of interest. Therefore system 10 may optionally include image database 18 to store image information relating to the patient's body. Image information may include, for example, a region of interest surrounding a destination site for medical device 24 and/or multiple regions of interest along a navigation path contemplated to be traversed by medical device 24. The data in image database 18 may comprise known image types including (1) one or more two-dimensional still images acquired at respective, individual times in the past; (2) a plurality of related two-dimensional images obtained in real-time from an image acquisition device (e.g., fluoroscopic images from an x-ray imaging apparatus), wherein the image database acts as a buffer (live fluoroscopy); and/or (3) a sequence of related two-dimensional images defining a cine-loop wherein each image in the sequence has at least an ECG timing parameter associated therewith, adequate to allow playback of the sequence in accordance with acquired real-time ECG signals obtained from ECG monitor 20. It should be understood that the foregoing embodiments are examples only and not limiting in nature. For example, the image database may also include three-dimensional image data as well. It should be further understood that the images may be acquired through any imaging modality, now known or hereafter developed, for example X-ray, ultra-sound, computerized tomography, nuclear magnetic resonance or the like.

ECG monitor 20 is configured to continuously detect an electrical timing signal of the heart organ through the use of a plurality of ECG electrodes (not shown), which may be externally-affixed to the outside of a patient's body. The timing signal generally corresponds to a particular phase of the cardiac cycle, among other things. Generally, the ECG signal(s) may be used by the control unit 12 for ECG synchronized play-back of a previously captured sequence of images (cine loop) stored in database 18. ECG monitor 20 and ECG-electrodes may both comprise conventional components.

Medical positioning system 22 is configured to serve as the localization system and therefore to determine position (localization) data with respect to one or more magnetic position sensors 28 and/or electrodes 30 and output a respective location reading. The location readings may each include at least one or both of a position and an orientation (P&O) relative to a reference coordinate system (e.g., magnetic based coordinate system, impedance based coordinate system), which may be the coordinate system of MPS 22. For some types of sensors, the P&O may be expressed with five degrees-of-freedom (five DOF) as a three-dimensional (3D) position (e.g., a coordinate in three perpendicular axes X, Y and Z) and two-dimensional (2D) orientation (e.g., a pitch and yaw) of a magnetic position sensor 28 in a magnetic field relative to a magnetic field generator(s) or transmitter(s) and/or electrode 30 in an applied electrical field relative to an electrical field generator (e.g., a set of electrode patches). For other sensor types, the P&O may be expressed with six degrees-of-freedom (six DOF) as a 3D position (e.g., X, Y, Z coordinates) and 3D orientation (e.g., roll, pitch, and yaw).

Medical positioning system 22 determines respective locations (e.g., P&O) in the reference coordinate system based on capturing and processing signals received from the magnetic position sensor 28 while the sensor is disposed in a controlled low-strength alternating current (AC) magnetic (e.g., magnetic) field and signals received from the electrode 30 while the electrodes are disposed in a controlled electrical field generated by electrode patches, for example.

Each magnetic position sensor 28 and the like may comprise a coil and, from an electromagnetic perspective, the changing or AC magnetic field may induce a current in the coil(s) when the coil(s) are in the magnetic field. The magnetic position sensor 28 is thus configured to detect one or more characteristics (e.g., flux) of the magnetic field(s) in which it is disposed and generate a signal indicative of those characteristics, which is further processed by medical positioning system 22 to obtain a respective P&O for the magnetic position sensor 28. The electrode 30 may comprise a ring electrode, in some examples. The electrode 30 can be configured to detect one or more characteristics (e.g., current) of the electrical field(s) in which it is disposed and generate a signal indicative of those characteristics, which is further processed by medical positioning system 22 to obtain a respective P&O for the plurality of electrode 30.

Referring still to FIG. 1, in an embodiment, medical positioning system 22 may determine the P&O of medical positioning system enabled medical device 24 according to certain physical characteristics of electromagnetic position sensor 28 and electrode 30 in addition to the signals received from magnetic position sensor 28 and electrode 30. Such characteristics may include predetermined calibration data, for example, indicative of or corresponding to the respective winding angles of one or more portions of a coil on sensor 28, the number of coil portions, the type(s) of conductor used in the coil, and the direction and number of loops in the coil. In addition, such characteristics may include predetermined calibration data, for example, indicative of or corresponding to a position of electrode 30, the number of electrodes 30, size of electrode 30, shape of electrode 30, and type of material(s) the electrodes are formed of. Medical positioning system 22 may have such characteristics of the magnetic position sensor 28 and/or electrode 30 pre-programmed, may determine such characteristics from a calibration procedure, or may receive such characteristics from a storage element coupled with medical device 24.

Magnetic position sensor 28 and the electrode 30 may be associated with medical positioning system enabled medical device 24. Another medical positioning system sensor, namely, patient reference sensor (PRS) 26 (if provided in system 10) can be configured to provide a positional reference of the patient's body so as to allow motion compensation for patient body movements, such as respirationinduced movements. Such motion compensation is described in greater detail in U.S. patent application Ser. No. 12/650,932, entitled "Compensation of Motion in a Moving Organ Using an Internal Position Reference Sensor", hereby incorporated by reference in its entirety as though fully set forth herein. PRS 26 may be attached to the patient's manubrium sternum or other location. Like the magnetic position sensor 28, PRS 26 can be configured to detect one or more characteristics of the magnetic field in which it is disposed, wherein medical positioning system 22 determines a location reading (e.g., a P&O reading) indicative of the PRS's position and orientation in the reference coordinate system. In some embodiments, an additional PRS can be configured to detect one or more characteristics of the electrical field in which it is disposed, wherein the medical positioning system 22 determines a location reading (e.g., a P&O reading) indicative of the PRS's position and orientation in the reference coordinate system.

Embodiments of the present disclosure can detect and correct impedance shift and/or drift, associated with the electrode 30. For example, impedance-based navigational systems can be subject to nonlinear shift and/or drift due to numerous physiologic phenomena (e.g., local conductivity changes due to saline or lesions, sweat/patch interactions, changes in lung filling, etc.). Magnetic navigational systems are not subject to these phenomena. By first registering the impedance based coordinate system with the magnetic based coordinate system, impedance shift and/or drift can be detected on a medical device with one or more magnetic position sensors 28 and one or more electrodes 30. Based on the detected shift and/or drift, the accuracy of the magnetic position sensor 28 and magnetic based coordinate system can be conveyed to the impedance based coordinate system. In some embodiments, magnetic position sensors 28 can be expensive to produce and can require more expensive support equipment to operate. Thus, impedance based medical devices that use impedance based sensors (e.g., electrodes 30) for navigation purposes can be preferred over magnetic position sensors 28. In addition, impedance based devices can be more ubiquitous than magnetic based devices, which can lead to a general preference for use of impedance based devices. Embodiments of the present disclosure can provide for navigation of an impedance based device with an accuracy comparable to that associated with a magnetic based device.

In addition, embodiments of the present disclosure can provide advantages over prior methods that use time to detect impedance shift and/or drift. For example, some prior methods are time dependent and detect impedance shift and/or drift based on large changes in impedance locations of electrodes over time (e.g., sudden changes in impedance locations of the electrodes). As such, it can be difficult to distinguish impedance shift and/or drift from manipulation of the electrode and/or catheter equipped with the electrode. For example, the catheter can be moved abruptly over a period of time. Prior methods can classify the abrupt movement as shift, since they rely on time. In addition, time dependent methods may not be able to detect a slow shift and/or drift associated with the impedance location of the electrode. Embodiments of the present disclosure can provide for shift and/or drift detection and/or correction that are time independent.

Figure 2:
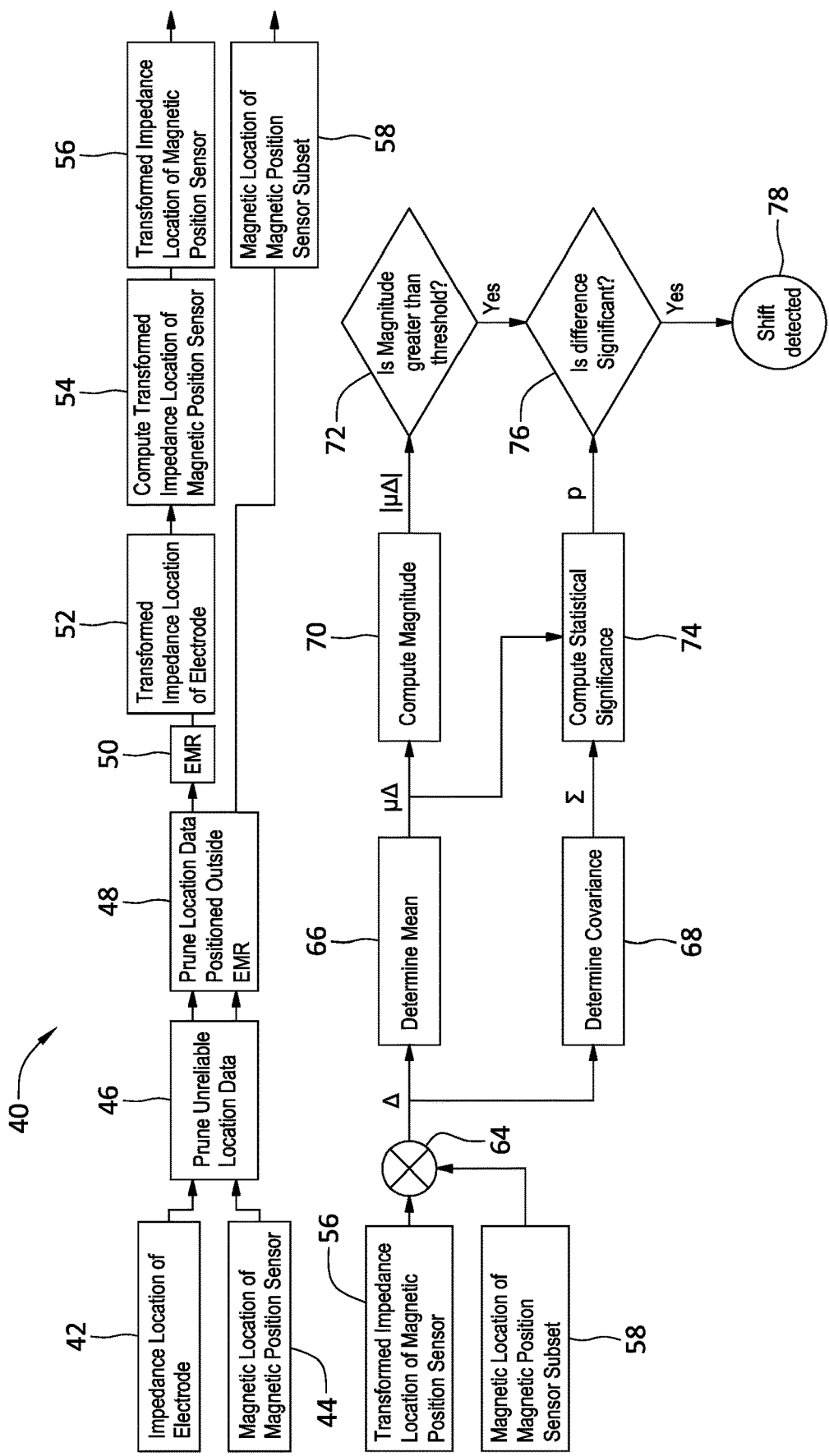
FIG. 2 depicts a flow diagram associated with impedance shift and/or drift detection, in accordance with embodiments of the present disclosure.

FIG. 2 depicts a flow diagram 40 associated with impedance shift and/or drift detection, in accordance with embodiments of the present disclosure. In some embodiments, the flow diagram 40 can represent a method for impedance shift and/or drift detection. The method can differentiate between events that appear to be an impedance shift and/or drift, but are not impedance shifts and/or drifts. The flow diagram 40 can include receiving an impedance location of an electrode 30 in an impedance based coordinate system, at box 42, and receiving a magnetic location of a magnetic position sensor 28 in a magnetic based coordinate system, at box 44. In some embodiments, the electrode 30 and the magnetic position sensor 28 can be disposed on a single catheter. For example, the magnetic position sensor 28 can be disposed on a distal end of the catheter and the electrode 30 can be disposed proximally on the catheter in relation to the magnetic position sensor 28. The electrode 30 can be positioned on the catheter such that it is disposed in an impedance based coordinate system (e.g., impedance field) and the magnetic position sensor can be positioned on the catheter such that it is disposed in a magnetic based coordinate system (e.g., magnetic field).

As discussed herein, the medical positioning system 22 can generate an electrical field in which the electrode 30 can be placed. The electrode 30 can generate an impedance signal based on the strength of the electrical field and the position of the electrode 30 in the electrical field. Based on the impedance signal, the impedance location of the electrode 30 can be determined in an impedance based coordinate system. The medical positioning system 22 can also generate a magnetic field in which the magnetic position sensor 28 can be placed. The magnetic location of the magnetic position sensor 28 can be computed based on a signal received from the magnetic position sensor 28. The signal can be generated by the magnetic position sensor 28 based on the strength of the magnetic field and the position and/or orientation of the magnetic position sensor 28 in the magnetic field.

In some embodiments, location data (e.g., impedance location of the electrode 30 and magnetic location of the magnetic position sensor 28) can be pruned at box 46. In an example, the impedance locations of electrodes 30 can be pruned for an unreliable impedance status or magnetic locations of the magnetic position sensors 28 can be pruned for an unreliable magnetic status. An unreliable status can refer to a union of data acquisition errors that may be detected in hardware and/or data quality indicators that have been detected in software (e.g., filter settling, excessive velocity of a catheter, in-sheath electrodes, ventilator gating, etc.). For impedance localization, examples of unreliable status can be patches that have been disconnected, in-sheath electrodes, excessive noise, saturation prior to demodulation and/or excessive velocity of a catheter. For magnetic localization, examples of unreliable status can be poor convergence, movement of a magnetic position sensor out of a motion box, and/or metal distortion caused to the magnetic field.

In some embodiments, the impedance locations of the electrodes 30 can be filtered based on a confidence metric associated with the impedance location of the electrodes 30. Filtering of the impedance locations of the electrodes 30 can provide a measure of where impedance locations can be accurately transformed into a magnetic location. The confidence metric can be based on the impedance locations of the electrodes 30 with respect to a location of the electromagnetic registration. In some embodiments, the confidence metric can be based on the impedance locations of the electrodes 30 with respect to a general location of the electromagnetic registration as a whole and/or particular regions of the electromagnetic registration, as discussed herein. In some embodiments, the confidence metric can be based on the impedance locations of the electrodes 30 with respect to one or more individual registration points that form the electromagnetic registration. In an example, in response to the impedance locations (e.g., coordinates) of the electrodes 30 being located outside of a location (e.g., coordinates) of the electromagnetic registration (e.g., volume of interest) a low confidence can be assigned to the impedance locations of the electrodes 30. In response to the low confidence metric assigned to the impedance locations of the electrodes 30, the impedance locations of the electrodes 30 can be filtered out. As a distance by which the impedance locations are located away from the electromagnetic registration increases, a value of the confidence metric can be decreased, in some embodiments.

In some embodiments, the confidence metric can be computed for a number of impedance locations in the impedance based coordinate system. For the impedance locations where the confidence metric is appropriate for transforming the impedance locations into corresponding magnetic locations, an isosurface can be displayed around regions where those impedance locations with the appropriate confidence metric are located. In an example, an electromagnetic registration can be constructed for the right atrium of the heart and the superior vena cava. Consequently, a confidence can be high in the right atrium and the superior vena cava. However, a confidence can be low in the distal coronary sinus. In some embodiments, a number of nearest registration points in the impedance based coordinate system can be identified and those registration points can be used as inputs to a weighted least squares fit of both a linear and a quadratic mapping from impedance based coordinates to magnetic based coordinates. As used herein, a number of refers to one or more. In some embodiments, weighting for the least squares fit can be chosen as a function of distance scaled such that it falls to zero at a distance of a farthest nearby point identified. In some embodiments, a Euclidian norm of the difference between the coefficient vectors of the linear and quadratic mappings can be computed. Where the Euclidian norm is small, nearby points can be determined to be dense enough to accurately measure a local linearization of the transformation of the impedance locations of the electrodes 30 to the magnetic space and a confidence of the transformation of the impedance locations of the electrodes 30 to the magnetic space can be high. Where the Euclidian norm is larger, additional registration points can be gathered (e.g., via a registration catheter).

In some embodiments, location data positioned outside of an electromagnetic registration can be pruned. In an example, the electromagnetic registration can be computed for a volume of interest in some embodiments. For instance, the electromagnetic registration can be generated for the left ventricle (e.g., first volume of interest) of the heart or a portion of the left ventricle. Thus, a majority, if not all location data collected within the left ventricle can be located within the electromagnetic registration. However, if location data is collected in the right atrium (e.g., second volume of interest located outside of the first volume of interest) when the electromagnetic registration has been generated for the left ventricle, the right atrium location data can be located outside of the electromagnetic registration generated for the left ventricle. As such, a determination could be made that an impedance shift has occurred, if the location data collected from the right atrium were used in detecting a shift. However, embodiments of the present disclosure can prune location data that is collected outside of the electromagnetic registration (e.g., for a first volume of interest).

In some embodiments, the electromagnetic registration can be treated as a nonlinear least-squares regression and confidence intervals can be computed for that regression. In some embodiments, confidence intervals can be computed for various regions of the electromagnetic registration. Each of the confidence intervals can include a particular width. For example, a high confidence region can be a region where a confidence interval width is less than a threshold (e.g., a 2 millimeter width). A low confidence region can be a region where the confidence interval width is greater than the threshold.

In some embodiments, magnetic coordinates associated with the magnetic locations of the magnetic position sensors 28 can be used to determine where the location data was collected. The magnetic position sensors 28 are not subject to impedance shift and thus the location data collected from them can be used to accurately determine from where the data was collected. The impedance locations of the electrodes 30 can be pruned based on the pruned magnetic locations of the magnetic position sensors 28 because the electrodes 30 and the magnetic position sensors 28 are disposed on the same catheter (e.g., registration catheter).

In some embodiments, the flow diagram 40 can include computing a transformed impedance location of the magnetic position sensor 28 using an electromagnetic registration between the impedance based coordinate system and the magnetic based coordinate system. The electromagnetic registration can be applied to the impedance locations of the electrodes 30 at box 50 and a transformed impedance locations of the electrodes 30 can be determined at box 52. In an example, the impedance locations of the electrodes 30 in the impedance based coordinate system can be transformed into transformed impedance locations of the electrodes 30 in the magnetic based coordinate system. Thus, the coordinates of the magnetic position sensors 28 and the transformed impedance locations of the electrodes 30 can both be located in the magnetic based coordinate system and can be directly compared with one another.

Based on the transformed impedance locations of the electrodes 30, transformed impedance locations of the magnetic position sensors 28 can be determined at box 54. In an example, based on a known physical relationship between the magnetic position sensors 28 and the electrodes 30 disposed on the catheter, the transformed impedance locations of the magnetic position sensors 28 can be determined in the magnetic based coordinate system using the transformed impedance locations of the electrodes 30. For instance, using specifications associated with the catheter (e.g., manufacturer specifications detailing the position of the electrodes 30 with respect to the magnetic position sensors 28), the transformed impedance locations of the magnetic position sensors 28 in the magnetic coordinate system can be determined. In some embodiments, using the specifications, the transformed impedance locations of the magnetic position sensors 28 can be positioned a particular distance (e.g., defined by the manufacturer's specifications) away from the transformed impedance locations of the electrodes 30. Thus, the transformed impedance locations of the magnetic position sensors 28 can be determined at box 54.

In some embodiments, a subset of the magnetic locations of the magnetic position sensors 28 that were not pruned at box 46 and box 48 (e.g., because they are located within the electromagnetic registration) can be compared with the transformed impedance locations of the magnetic position sensors at box 64. In an example, a difference (e.g., delta ($\Delta$)) can be determined between coordinates of the transformed impedance location of the magnetic position sensors 28 and respective coordinates of the magnetic locations of the magnetic position sensors 28 that were not pruned. In some embodiments, the difference between the coordinates of the transformed impedance location of the magnetic position sensors 28 and the respective coordinates of the magnetic locations of the magnetic position sensors 28 that were not pruned can be scalar and/or the difference can be a vector. In some embodiments, the delta between the coordinates of the transformed impedance locations of the magnetic position sensors 28 and respective coordinates of the magnetic locations of the magnetic position sensors 28 that were not pruned can be representative of any existing impedance shift. For example, because the transformed impedance locations of the magnetic position sensors 28 is determined based off of a known physical relationship with respect to the transformed impedance locations of the electrodes 30, which are susceptible to impedance shift; impedance shift that is present can be translated to the magnetic coordinate system via the transformed impedance locations of the electrodes 30.

In some embodiments, the flow diagram 40 can include determining a mean ($\mu_\Delta$) of the delta over a first time scale at box 66 and determining a covariance of the delta over a second time scale at box 68. In some embodiments, as discussed herein, the difference between the coordinates of the transformed impedance location of the magnetic position sensors 28 and the respective coordinates of the magnetic locations of the magnetic position sensors 28 that were not pruned can be scalar and/or the difference can be a vector. In an example, when the difference between the coordinates of the transformed impedance location of the magnetic position sensors 28 and the respective coordinates of the magnetic locations of the magnetic position sensors 28 that were not pruned is a vector, the covariance of the delta can be a full symmetric matrix. In some embodiments, the second time scale can be a longer time scale than the first time scale. In some embodiments, the determination of the mean of the delta over the first time scale at box 66 and the determination of the covariance of the delta over the second time scale at box 68 can be used to determine whether an impedance shift is consistent and not a transient impedance shift. If an impedance shift is transient, it may not be desirable to establish that a shift has been detected. For example, if it is established that an impedance shift exists as a result of the transient shift, a correction may be made for the impedance shift, which can provide for computation of incorrect locations of the electrodes 30 when the transient shift goes away.

In some embodiments, determination of the covariance of the delta over the second time scale can include determining the covariance of the delta using a long running covariance. In an example, the long running covariance can be used to measure how much the delta is changing at any point in time. Phenomena that can change the delta can include breathing of the patient and/or noise in instrumentation, for example. These occurrences, in some embodiments, can result in an increased covariance. In an example, the covariance can be computed over a longer time scale in a range from 30 to 180 seconds to capture the slower moving phenomena such as breathing. For example, if the longer time scale is not used, slower moving phenomena such as breathing may not be captured. However, to respond to impedance shifts rapidly, a shorter time scale in a range from 0.5 to 10 seconds can be used in determination of the mean.

In some embodiments, a magnitude of the mean of the delta ($|\mu_\Delta|$) over the first time scale can be computed at box 70. In an example, the first time scale can be a shorter time scale of the first and second time scale. The magnitude of the mean of the delta can be computed to determine if the impedance shift is large enough to clinically pose an issue. In an example, the magnitude of the mean of the delta can be compared to a threshold, in some embodiments, at box 72. In some embodiments, a determination of whether the magnitude of the mean of the delta exceeds the threshold can be made. For example, if the magnitude of the mean of the delta is less than the threshold, then a determination can be made that the impedance shift is clinically insignificant and a shift may not be detected. Alternatively, if the magnitude of the mean of the delta is greater than the threshold, then a determination can be made that the impedance shift is clinically significant and a shift may be detected. By ensuring that that the magnitude of the mean of the delta is greater than the threshold before detecting a shift, fewer distractions can be provided to a physician. For example, fewer indications that a shift has been detected can be provided to the physician, thus providing fewer interruptions to the physician while a procedure is being performed by the physician. In some embodiments, the threshold can be adjustable by the physician to accord with the physician's personal preference, as it may vary from physician to physician. For example, the threshold can be lowered such that indications of smaller impedance shifts are displayed to the physician and/or the threshold can be raised such that only indications of larger impedance shifts can be displayed to the physician.

In some embodiments, a norm, such as a Euclidean norm of the impedance location of the magnetic position sensor 28 and the magnetic location of the magnetic position sensor 28 can be computed and/or a distance between the impedance location of the magnetic position sensor 28 and the magnetic location of the magnetic position sensor 28 can be computed to determine if the impedance shift is large enough to clinically pose an issue.

In some embodiments, a statistical significance can be computed based on the mean of the delta and the covariance of the delta at box 74. The statistical significance (p) can be computed using the t-test. By computing the statistical significance, a determination of whether the impedance shift is statistically significant can be made at box 76. In an example, the statistical significance can be compared to a threshold, in some embodiments, at box 76. In some embodiments, a determination of whether the statistical significance exceeds the threshold can be made. For example, if the statistical significance is less than the threshold, then a determination can be made that the impedance shift is clinically insignificant and a shift may not be detected. Alternatively, if the statistical significance is greater than the threshold, then a determination can be made that the impedance shift is clinically significant and a shift may be detected at box 78. Thus, the statistical significance can be used to determine whether an impedance shift is statistically significant, or if it falls within a noise of what can be usually expected (e.g., instrumentation noise). As previously discussed, the threshold can be adjusted by the physician to accord with her/his own personal preference. In some embodiments, the statistical significance of the difference can be evaluated by comparing an average covariance of the difference computed over a long period of time (e.g., 30 to 180 seconds) with chi-square distribution. In some embodiments, if the covariance exceeds $X^2$, the shift can be declared.

In some embodiments, determining the statistical significance can include normalizing the mean of the delta by the covariance of the delta. If the mean and variance are scalars, the mean squared can be divided by the variance. When the delta is a vector, Hotelling's T-squared statistic can be used and the mean can be multiplied by the inverse of the covariance, which can then be multiplied by the transpose of the mean. In both scalar and vector cases, Chi-squared distribution can be used to test for significance.

In some embodiments, if an impedance shift is detected, an indication that a corrective action should be taken can be provided to the physician. The corrective action can include collecting additional location data, in some embodiments, to create a new electromagnetic registration, which can account for the detected shift. For example, the corrective action can include collecting additional location data to build a secondary electromagnetic registration to account for the detected shift, as detailed in the application, titled "Electromagnetic Dynamic Registration for Device Navigation", filed 20 Jun. 2016 and in the application, titled "Electromagnetic Dynamic Registration for Device Navigation", filed 20 Jun. 2016, which are both hereby incorporated by reference in their entirety.

Figure 3:
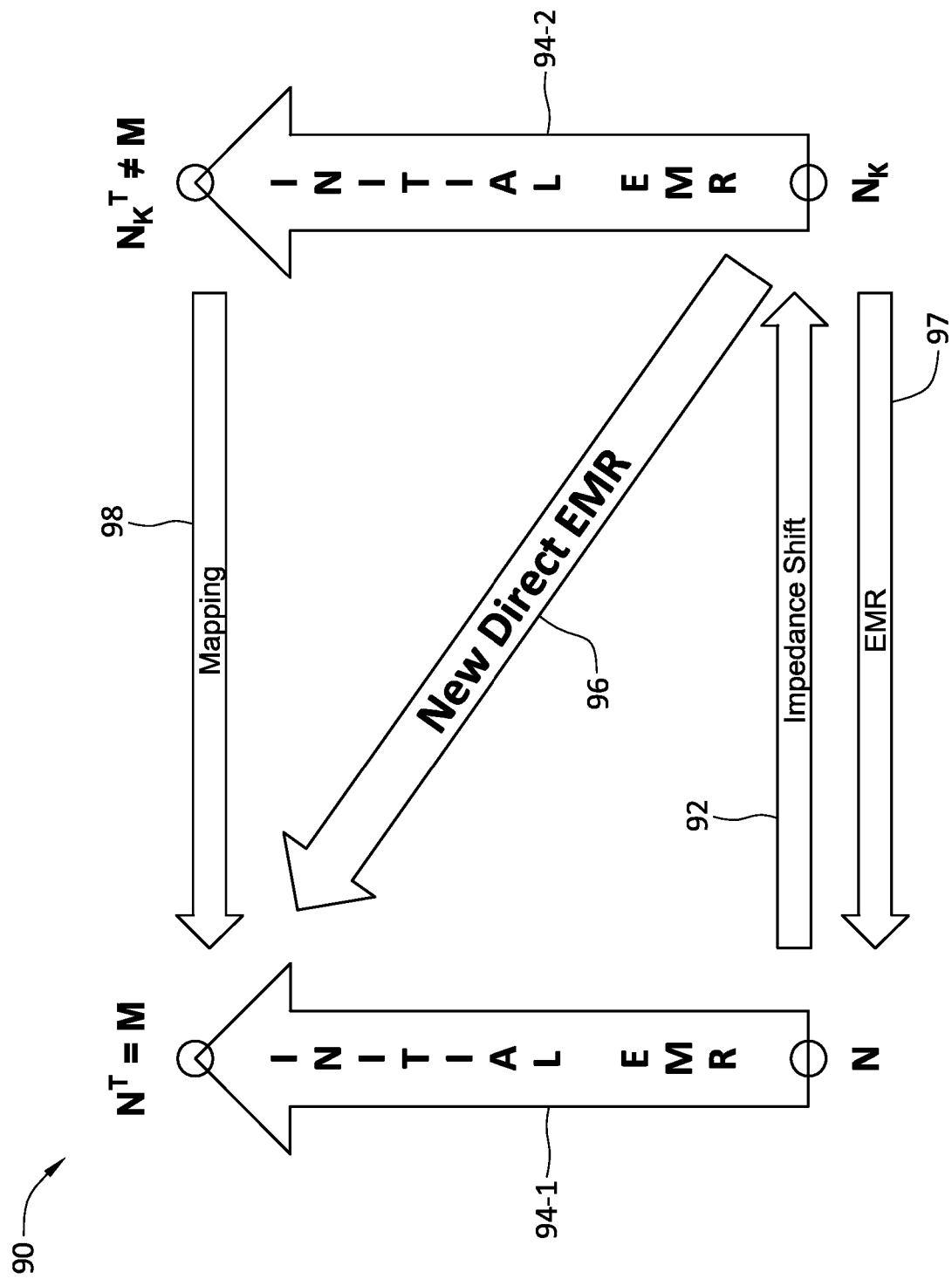
FIG. 3 depicts a flow diagram associated with impedance shift and/or drift correction, in accordance with embodiments of the present disclosure.

FIG. 3 depicts a flow diagram 90 associated with impedance shift and/or drift correction, in accordance with embodiments of the present disclosure. In some embodiments, a shifted impedance location of an electrode 30 in a shifted impedance based coordinate system can be received. As discussed herein, various factors can cause a location of the electrode 30 in the impedance based field to undergo shift (e.g., shift and/or drift). In some embodiments, when a physician is navigating a catheter and/or collecting data points (e.g., for mapping a volume of interest) based on the impedance locations of the electrodes 30 in the impedance based field, the impedance locations of the electrodes 30 can be shifted as a result of shift inducing phenomena, as discussed herein. Thus, the impedance locations of the electrodes 30 can be shifted from the actual location of the electrodes 30. As such, embodiments of the present disclosure can include registering the impedance based coordinate system with the magnetic based coordinate system, which is not susceptible to shift, and correcting for shifted impedance locations of the electrodes 30 based on the registration (e.g., electromagnetic registration).

In some embodiments, a shifted impedance location of an electrode 30 can be received in a shifted impedance based coordinate system. For example, the shifted impedance location of the electrode 30 can be represented as $N_K$ in the flow diagram 90, where K is any time. The impedance shift can be represented by impedance shift 92, which has shifted the impedance location of the electrode 30, represented as N to a shifted impedance location of the electrode 30 $N_K$. As such, navigation based on the impedance location N of the electrode 30 can be skewed as a result of the impedance shift 92 of the electrode 30. In some embodiments, the shifted impedance location can be transformed from the impedance based coordinate system to the magnetic based coordinate system through application of an electromagnetic registration 94-1, 94-2. Application of the initial EMR 94-2 results in an erroneous impedance location $N_K^T$, which can be further mapped to the magnetic coordinate system, as discussed herein. In some embodiments, as detailed in the application, titled "Electromagnetic Dynamic Registration for Device Navigation", filed 20 Jun. 2016 and in the application, titled "Electromagnetic Dynamic Registration for Device Navigation", filed 20 Jun. 2016, which are both hereby incorporated by reference in their entirety, the electromagnetic registration can be generated and the electromagnetic registration can be an electromagnetic dynamic registration.

In some embodiments, the electromagnetic registration 94-1, 94-2 can be used to transform the impedance location of the electrode 30 to the magnetic coordinate system generated for an impedance shift 92 that has occurred. In some embodiments, when the impedance location N of the electrode 30 has been shifted due to an impedance shift 92, a new direct electromagnetic registration (New Direct EMR) 96 can be generated between the shifted impedance based coordinate system and the magnetic based coordinate system based on the impedance shift 92 associated with the shifted impedance location $N_K$ of the electrode 30. In an example, the new direct electromagnetic registration 96 can be a secondary electromagnetic registration, which can be determined by collecting an additional number of fiducial points (e.g., registration points), as detailed in the application, titled "Electromagnetic Dynamic Registration for Device Navigation", filed 20 Jun. 2016 and in the application, titled "Electromagnetic Dynamic Registration for Device Navigation", filed 20 Jun. 2016, which are both hereby incorporated by reference in their entirety.

In some embodiments, the electromagnetic registration can be applied to transform the shifted impedance location $N_K$ of the electrode 30 from the shifted impedance based coordinate system into an unshifted magnetic location of the electrode 30 in the magnetic based coordinate system, using the electromagnetic registration. In some embodiments, application of the electromagnetic registration can include applying the new electromagnetic registration to the shifted impedance location $N_K$. Thus, application of the new direct electromagnetic registration can compute a shift corrected location $N^T$ of the electrode 30. In an example, the shift corrected location $N^T$ can be computed in the magnetic based coordinate system and the shift corrected location $N^T$ can be consistent with and/or equal to a magnetic location (M) of the magnetic position sensor 28 (e.g., $N^T=M$). For example, the shift corrected location $N^T$ of the electrode 30 can be displayed in a correct location with respect to the magnetic position sensor 28 (e.g., based on manufacturer's specifications).

If the new direct electromagnetic registration 96 is not generated and the initial electromagnetic registration 94-2 is applied to the shifted impedance location $N_K$ of the electrode 30, without further processing steps (discussed below), the transformed impedance location $N_K^T$ will not be consistent and/or equal to the magnetic position M of the magnetic position sensor 28, because the initial electromagnetic registration was generated before the impedance shift took place and does not account for the impedance shift.

In some embodiments, in response to the impedance shift 92, the shifted impedance location $N_K$ can be transformed to a pre-shifted impedance location (N) of the electrode 30 via electromagnetic registration (EMR) 97. In an example, a shift that has occurred can be subtracted from the shifted impedance location $N_K$ and the shifted impedance location can be transformed to the pre-shifted impedance location N of the electrode 30. In some embodiments, a pre-shifted electromagnetic registration (e.g., initial electromagnetic registration 94-1) can be applied to the pre-shifted impedance location of the electrode 30 to transform the pre-shifted impedance location of the electrode 30 into the shift corrected location of the electrode 30 in the magnetic based coordinate system, such that $N^T=M$, as discussed herein. In some embodiments, the shifted impedance location $N_K$ of the electrode 30 in the impedance field can be transformed to the unshifted impedance field using magnetic position sensors 28 as a reference, since the magnetic position sensors 28 are not susceptible to impedance shift, and using an inverse mapping technique, as detailed in application publication number WO2014028114, titled Correction of Shift and Drift in Impedance-based Medical Device Navigation Using Magnetic Field Information. For example, an inverse of the initial electromagnetic registration 94-1 can be applied to the magnetic location of the magnetic position sensor 28 to approximate N. If the inverse of the initial electromagnetic registration 94-1 is denoted as $M^{-T}$, then $N_K$ can be transformed via $M^{-T}$, which can then be transformed by $M^{(-T)^T}$, which is equal to M.

In some embodiments, a pre-shifted electromagnetic registration (e.g., initial electromagnetic registration 94-2) can be applied to the shifted impedance location $N_K$ of the electrode to transform the shifted impedance location $N_K$ into a shifted transformed impedance location $N_K^T$ of the electrode 30, where $N_K^T \neq M$. For example, the shifted impedance location $N_K$ can be transformed from the shifted impedance field to a shifted transformed impedance field in magnetic space with the pre-shifted electromagnetic registration 94-2. In some embodiments, the initial registration 94-1 and the initial registration 94-2 can be the same registration, but are displayed as separate arrows for simplicity. In some embodiments, a mapping 98 (e.g., transformation) between a magnetic based coordinate system and a shifted transformed impedance based coordinate system can be applied to the shifted transformed impedance location of the electrode 30 to determine the shift corrected location of the electrode 30, such that $N^T = M$.

The shifted impedance location $N_K$ can be transformed to $N^T$ such that $N^T = M$ using an electromagnetic registration, whether it is an initial electromagnetic registration 94-1, 94-2, or a new direct electromagnetic registration 96, such that $N^T = M$. Embodiments of the present disclosure can dynamically adapt to additional occurrences of shifts. For example, additional corrections can be computed and convolved together as though they were layered transformations, resulting in a determination of shift corrected impedance locations of the electrodes 30.

Figure 4:
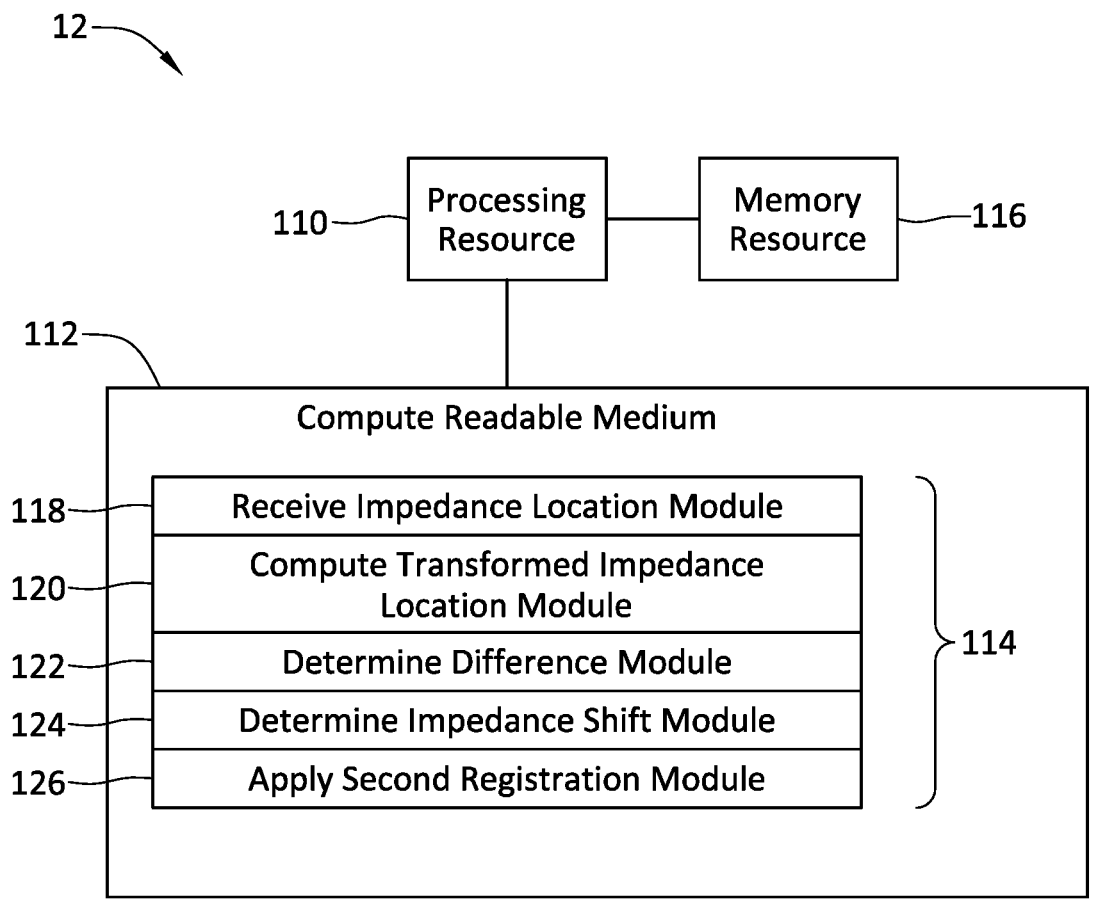
FIG. 4 depicts a block diagram of an example of a computer-readable medium in communication with processing resources of a computing device, in accordance with embodiments of the present disclosure.

FIG. 4 depicts a block diagram of an example of a computer-readable medium 162 in communication with processing resources 110 of a computing device, in accordance with embodiments of the present disclosure. The main control 12, as discussed in relation to FIG. 1, can utilize software, hardware, firmware, and/or logic to perform a number of functions. The main control 12 can include a number of remote computing devices.

The main control 12 can be a combination of hardware and program instructions configured to perform a number of functions. The hardware, for example, can include one or more processing resources 110, computer readable medium (CRM) 112, etc. The program instructions (e.g., computer-readable instructions (CRI) 114) can include instructions stored on CRM 112 and executable by the processing resource 110 to implement a desired function (e.g., apply a second electromagnetic registration, in response to the determination that the impedance shift exists, to transform the impedance location of the electrode from a shifted impedance based coordinate system into a shift corrected location of the electrode in the magnetic based coordinate system, using the electromagnetic registration, etc.). The CRI 114 can also be stored in remote memory managed by a server and represent an installation package that can be downloaded, installed, and executed. The main control 12 can include memory resources 116, and the processing resources 110 can be coupled to the memory resources 116.

Processing resources 110 can execute CRI 114 that can be stored on an internal or external non-transitory CRM 112. The processing resources 110 can execute CRI 114 to perform various functions, including the functions described herein.

A number of modules 118, 120, 122, 124, 126, can be sub-modules or other modules. For example, the receive impedance location module 118 and the compute transformed impedance location module 120 can be sub-modules and/or contained within a single module. Furthermore, the number of modules 118, 120, 122, 124, 126 can comprise individual modules separate and distinct from one another.

A receive impedance location module 118 can comprise CRI 114 and can be executed by the processing resource 110 to receive an impedance location of an electrode 30 in an impedance based coordinate system and a magnetic location of a magnetic position sensor 28 in a magnetic based coordinate system. In some embodiments, the electrode 30 and the magnetic position sensor 28 can be disposed on a same catheter (e.g., a registration catheter).

A compute transformed impedance location module 120 can include CRI 114 and can be executed by the processing resource 110 to compute a transformed impedance location of the magnetic position sensor 28 using a first electromagnetic registration between the impedance based coordinate system and the magnetic based coordinate system. The transformed impedance location of the magnetic position sensor 28 can be computed in a similar manner as that discussed in relation to FIG. 2. For example, based on a known physical relationship between the magnetic position sensors 28 disposed on the catheter and the electrodes 30, the transformed impedance locations of the magnetic position sensors 28 can be determined in the magnetic based coordinate system using the transformed impedance locations of the electrodes 30.

A determine difference module 122 can include CRI 114 and can be executed by the processing resource 110 to determine a difference between the transformed impedance location of the magnetic position sensor and the magnetic location of the magnetic position sensor. Some embodiments can include determining a mean of the difference over a first time scale and determining a covariance of the difference over a second time scale. In some embodiments, the determination of the mean of the difference over the first time scale and the determination of the covariance of the difference over the second time scale can be used to determine whether an impedance shift is consistent and not a transient impedance shift.

A determine impedance shift module 124 can include CRI 114 and can be executed by the processing resource 110 to determine that an impedance shift exists based on the difference between the transformed impedance location of the magnetic position sensor and the magnetic location of the magnetic position sensor. In some embodiments, a magnitude of a mean of the difference can be determined and a statistical significance can be determined based on the mean of the difference between the transformed impedance location of the magnetic position sensor and the magnetic location of the magnetic position sensor and the covariance of the difference. Based on the magnitude of the mean of the difference and the statistical significance, a determination of whether a shift exists can be made.

An apply second registration module 126 can include CRI and can be executed by the processing resource 110 to apply a second electromagnetic registration, in response to the determination that the impedance shift exists, to transform the impedance location of the electrode from a shifted impedance based coordinate system into a shift corrected location of the electrode in the magnetic based coordinate system, using the electromagnetic registration. In some embodiments, the first electromagnetic registration can be the same as the second electromagnetic registration, and a shift can be performed before or after application of the electromagnetic registration, as discussed in relation to FIG. 3. In some embodiments, the first electromagnetic registration can be a pre-shifted electromagnetic registration and the second electromagnetic registration can be a new direct electromagnetic registration, as discussed in relation to FIG. 3.

Embodiments are described herein of various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment(s) is included in at least one embodiment. Thus, appearances of the phrases "in various embodiments," "in some embodiments," "in one embodiment," or "in an embodiment," or the like, in places throughout the specification, are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features, structures, or characteristics of one or more other embodiments without limitation given that such combination is not illogical or non-functional.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Although at least one embodiment for impedance shift and drift detection and correction has been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the devices. Joinder references (e.g., affixed, attached, coupled, connected, and the like) are to be construed broadly and can include intermediate members between a connection of elements and relative movement between elements. As such, joinder references do not necessarily infer that two elements are directly connected and in fixed relationship to each other. It is intended that all matter contained in the above description or shown in the accompanying drawings shall be interpreted as illustrative only and not limiting. Changes in detail or structure can be made without departing from the spirit of the disclosure as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed:

1. A method for correction of an impedance shift in an impedance based coordinate system, comprising:
   generating a second electromagnetic registration in response to a detected impedance shift based on fiducial points created by applying an inverse of a pre-shifted electromagnetic registration to magnetic locations of the magnetic position sensor in combination with shifted impedance locations of the electrode;
   receiving a subsequent shifted impedance location of an electrode in a shifted impedance based coordinate system;
   applying the second electromagnetic registration generated after the impedance shift is detected to transform the subsequent shifted impedance location of the electrode to a pre-shifted impedance location of the electrode; and
   applying the pre-shifted electromagnetic registration to the pre-shifted impedance location of the electrode to transform the pre-shifted impedance location of the electrode into a shift corrected location of the electrode in a magnetic based coordinate system, and the shift corrected location is consistent with a magnetic location of a magnetic position sensor in the magnetic based coordinate system, wherein the pre-shifted electromagnetic registration is generated before the impedance shift is detected.

2. The method of claim 1, wherein transforming the shifted impedance location of the electrode to the pre-shifted impedance location of the electrode includes transforming the shifted impedance location of the electrode using the magnetic location of the magnetic position sensor.

3. A method for detection and correction of an impedance shift in an impedance based coordinate system, comprising:
   receiving an impedance location of an electrode in an impedance based coordinate system and a magnetic location of a magnetic position sensor in a magnetic based coordinate system;
   computing a transformed impedance location of the magnetic position sensor using a first electromagnetic registration between the impedance based coordinate system and the magnetic based coordinate system;

determining a difference between the transformed impedance location of the magnetic position sensor and the magnetic location of the magnetic position sensor;

determining that an impedance shift exists based on the difference between the transformed impedance location of the magnetic position sensor and the magnetic location of the magnetic position sensor; and applying a second electromagnetic registration, in response to the determination that the impedance shift exists, to transform the impedance location of the electrode from a shifted impedance based coordinate system into a shift corrected location of the electrode in the magnetic based coordinate system, using the second electromagnetic registration, wherein determining the difference between the transformed impedance location of the magnetic position sensor and the magnetic location of the magnetic position sensor includes determining a mean of the difference over a first time scale and determining a covariance of the difference over a second time scale.

4. The method of claim 3, further comprising determining whether an impedance shift is a transient impedance shift based on the mean of the difference over the first time scale and the covariance of the difference over the second time scale.

5. The method of claim 3, wherein the electrode and the magnetic position sensor are disposed on a same catheter.

6. The method of claim 3, further comprising providing an indication to a user to take corrective action in response to determining that the impedance shift exists.

7. The method of claim 3, wherein applying the second electromagnetic registration to transform the impedance location of the electrode to the shift corrected location comprises:

transforming the impedance location of the electrode to a pre-shifted impedance location of the electrode using the second electromagnetic registration; and applying the first electromagnetic registration to the pre-shifted impedance location of the electrode to transform the pre-shifted impedance location of the electrode into the shift corrected location of the electrode in the magnetic based coordinate system.

8. The method of claim 3, wherein applying the second electromagnetic registration to transform the impedance location of the electrode into the shift corrected location comprises:

applying the first electromagnetic registration to the impedance location of the electrode to transform the impedance location into a shifted transformed impedance location of the electrode; and applying a mapping between a pre-shifted transformed impedance based coordinate system and a shifted transformed impedance based coordinate system to the transformed impedance location of the electrode under the second electromagnetic registration to determine the shift corrected location of the electrode in the magnetic based coordinate system.

* * * * *